United States Patent [19]

Castiglia

[11] 4,085,746
[45] Apr. 25, 1978

[54] ANKLE WRAP

[75] Inventor: Ignatius F. Castiglia, New York, N.Y.

[73] Assignee: Lenox Hill Brace Shop, Inc., New York, N.Y.

[21] Appl. No.: 724,495

[22] Filed: Sep. 20, 1976

[51] Int. Cl.² .............................................. A61F 13/06
[52] U.S. Cl. ............................. 128/166; 128/DIG. 15
[58] Field of Search ............ 128/166, 165, 169, 166.5, 128/157, 80 H, DIG. 15

[56] References Cited

U.S. PATENT DOCUMENTS

| | | | |
|---|---|---|---|
| 2,484,130 | 10/1949 | Thibault | 128/166 |
| 3,255,749 | 6/1966 | Smithers | 128/169 |
| 3,674,023 | 7/1972 | Mann | 128/166 |
| 3,699,959 | 10/1972 | Garrahan et al. | 128/166 |
| 3,880,161 | 4/1975 | Fossel | 128/169 X |

Primary Examiner—John D. Yasko

Attorney, Agent, or Firm—Blum, Moscovitz, Friedman & Kaplan

[57] ABSTRACT

An improved reusable ankle wrap for effectively bracing an ankle without unduly restricting the ankle from walking and running motions and other athletic movements is provided. The ankle wrap includes an elongated elastic panel having a first fastening member secured to a first end portion thereof. A second fastening member is carried by the panel at a position spaced apart from the first fastening member to releasably engage the first fastening member when the portion of the elongated panel between said first and second fastening members is wrapped around the medial aspect of the longitudinal arch of a foot, the panel including further fastening members disposed at the other end portion thereof for releasably securably fastening the panel about an ankle and arch after the panel has been alternately wrapped about the ankle and medial aspect of the longitudinal arch in a predetermined manner.

12 Claims, 9 Drawing Figures

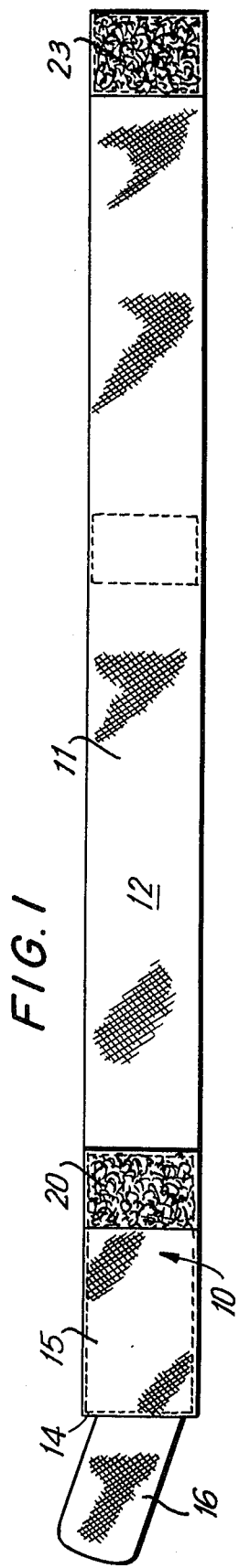
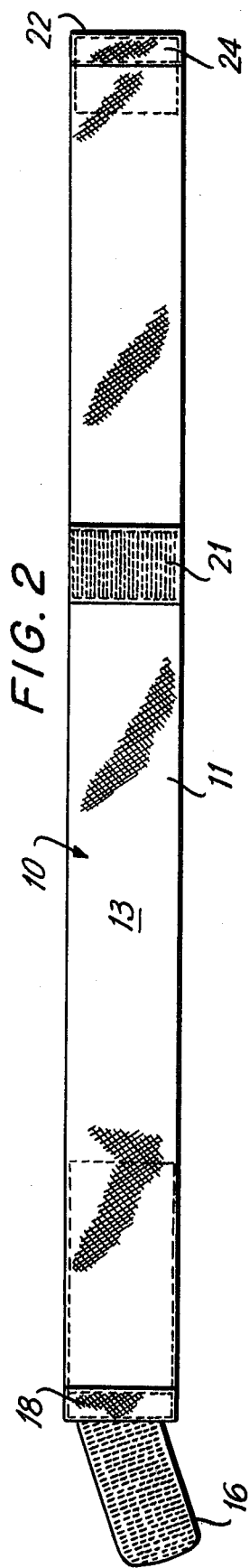
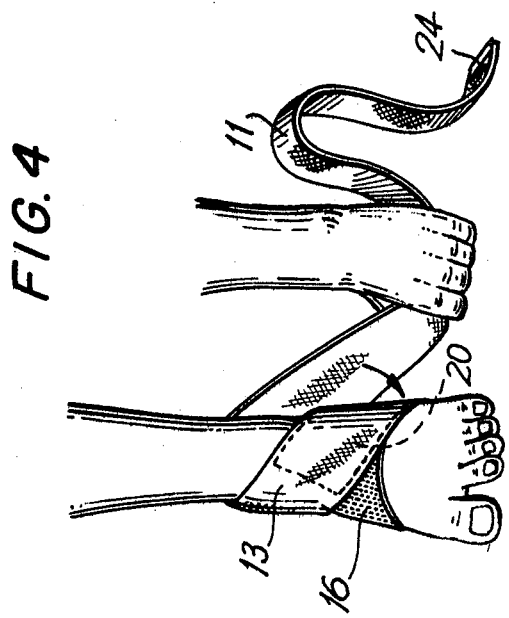
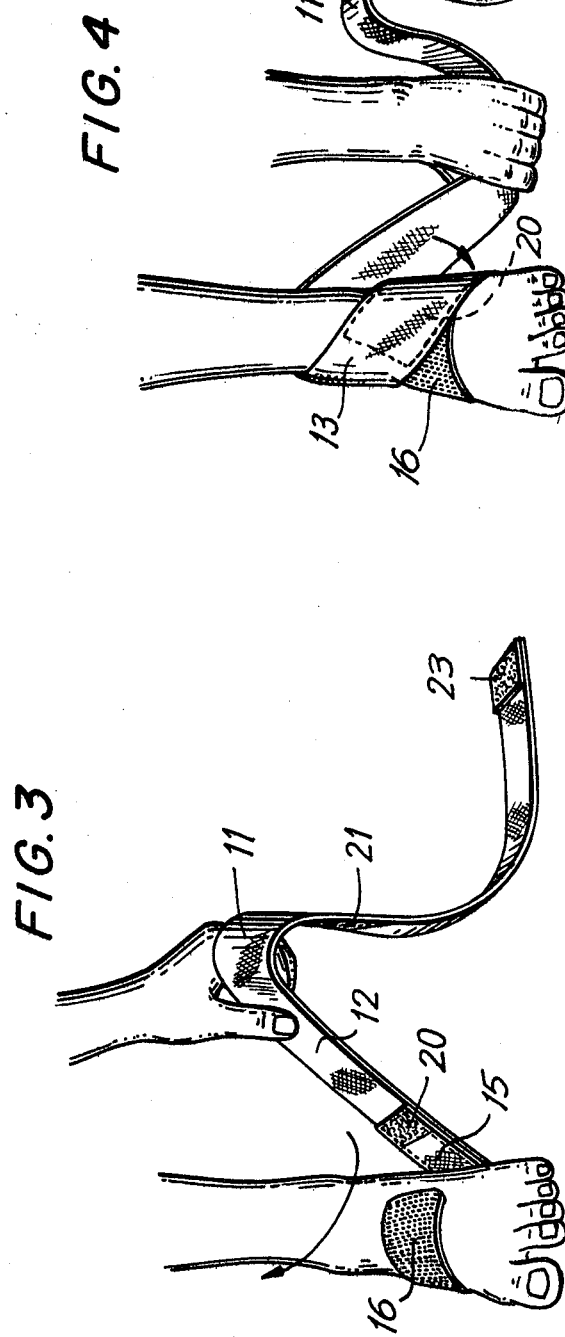

ANKLE WRAP

BACKGROUND OF THE INVENTION

This invention is directed to an improved ankle wrap and in particular to an improved ankle wrap in the form of an elongated elastic panel having fastening members selectively disposed along the lengthwise extent thereof for permitting wrapping of the ankle and instep in a predetermined manner.

Heretofore, ankle supports of the type utilized by athletes both during training and during competition and for medical purposes such as the rehabilitation of ankle sprains, have taken on various forms. Such ankle support devices have attempted to replace the "tape job" used by professional athletes whereby a web bandage and adhesive tape are utilized to wrap and tape an ankle. Ankles that are supported by a "tape job" when done by trained personnel are effectively braced. Moreover, such "tape jobs" are light and not bulky. However, since new tape must be utilized each time the ankle is wrapped, and additionally trained personnel are required to effect such taping, supporting an ankle by utilizing a "tape job" is expensive, time consuming and hence less than completely satisfactory.

Although reusable ankle supports have been developed, such ankle supports, at best, provide limited bracing. For example, those prior art ankle supports utilizing elastic wrapping materials often provide unwanted constriction to desired walking and running movement of the ankle required by an athlete without providing sufficient bracing of the ankle. Accordingly, an elastic ankle support for effectively bracing an ankle joint without restricting the walking and running movements required in athletic competition is desired.

SUMMARY OF THE INVENTION

Generally speaking, in accordance with the instant invention, an improved ankle wrap for effectively bracing an ankle is provided. The wrap is comprised of an elongated elastic panel having a first fastening member secured to a first elongated end portion of the panel. A second fastening member adapted to be releasably secured with the first fastening member is secured to the panel at a position spaced apart from the first fastening member to releasably engage the first fastening member when the portion of the elongated panel between the first fastening member and second fastening member is wrapped around the medial aspect of the longitudinal arch of a foot. Further fastening members are disposed at the other elongated end portion of the elastic panel for releasably securably fastening the panel about the ankle and arch after the panel has been alternately wrapped about the ankle and medial aspect of the longitudinal arch in a predetermined manner.

The predetermined manner of wrapping the improved ankle wrap of the instant invention is characterized by the repeated wrapping of the elongated elastic panel up and around the front of the ankle, behind the ankle and under the medial aspect of the longitudinal arch of the foot to thereby insure that blood circulation in the foot remains substantially unimpeded by the wrapping of the ankle in accordance with the instant invention.

Accordingly, it is an object of the instant invention to provide an improved ankle wrap for providing a high degree of support to an ankle.

A further object of the instant invention is to provide reusable ankle support capable of effectively bracing an ankle.

Still a further object of the instant invention is to provide an improved ankle wrap that avoids excessive constriction of the ankle.

Still a further object of the instant invention is to provide an elastic ankle wrap for providing effective support to an ankle without restricting walking and running movements of an ankle.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a front plan view of an ankle wrap constructed in accordance with a preferred embodiment of the instant invention;

FIG. 2 is a rear plan view of the ankle wrap depicted in FIG. 1; and

FIGS. 3 through 9 illustrate the manner in which an ankle is wrapped in accordance with the instant invention by the ankle wrap depicted in FIGS. 1 and 2.

DETAILED DESCRIPTION OF THE PREFERRED EMBODIMENTS

Figure 5:
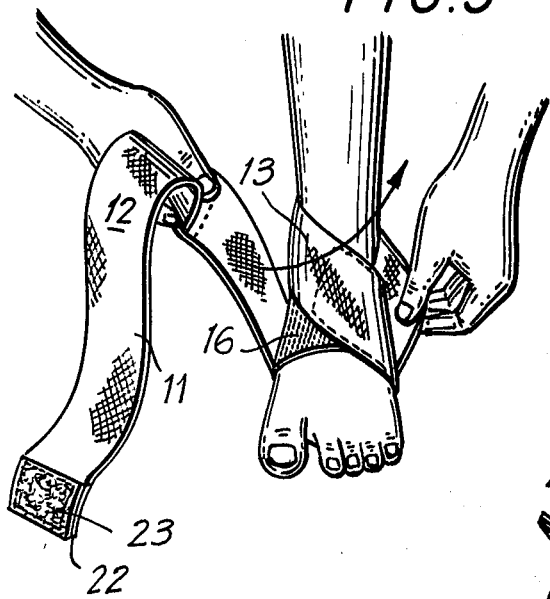

Reference is now made to FIGS. 1 and 2 of the drawings, wherein an ankle wrap, generally indicated as 10, is depicted. The ankle wrap is comprised of a elongated elastic panel 11 having a front surface 12 and a back surface 13. A nylon panel 15 is secured to the front surface 12 of the elastic panel 11 at a first end 14 and is coextensive with and defines a first end portion of the elastic panel. In a preferred embodiment, the nylon panel as well as the additional means carried by the elastic panel are secured to the elastic panel by being sewn thereto. However, other conventional adhesive means can be used for securing the nylon panel and other fastener means to the elastic panel 11.

Secured to the first end 14 of the elongated panel 11 on the back surface 13 thereof is a male Velcro fastening tab 16. An additional nylon reinforcing panel 18 can be provided coextensive with the end edge of the elastic panel for insuring that the male Velcro fastening tab 16 is securely fastened to the panel 11. A female Velcro fastening member 20 is disposed on the front surface 12 of the panel 11 and overlaps at least a portion of the nylon panel 15 so that the fastening member 20 is spaced apart from the male Velcro fastening tab 16 in order to permit same to effect a Velcro releasable fastening arrangement with the male Velcro fastening tab 16 when the nylon panel 15 is wrapped about the medial aspect of the longitudinal arch of a foot, hereinafter referred to as the "medial arch", in a manner to be discussed in greater detail below.

A further male Velcro fastening pad 21 is secured to the back surface 13 of the elongated panel 11 at a predetermined distance from the other end 22 of the elastic panel 11. A further female Velcro fastening pad 23 is secured to the front surface 12 of the elastic panel 11 and is coextensive with the end portion of the panel at the other end 22 thereof. As is detailed below, the female Velcro fastening pad 23 is provided for engaging the male Velcro fastening pad 21 when an ankle is wrapped in accordance with the instant invention to thereby releasably securably fasten the panel about the ankle and medial arch to effect bracing of the ankle. Finally, a panel 24 is provided coextensive with the end edge of the panel at the other end 22 thereof in order to reinforce same at the point that the panel is more likely to be grabbed when wrapping is to be effected thereby.

Figure 6:
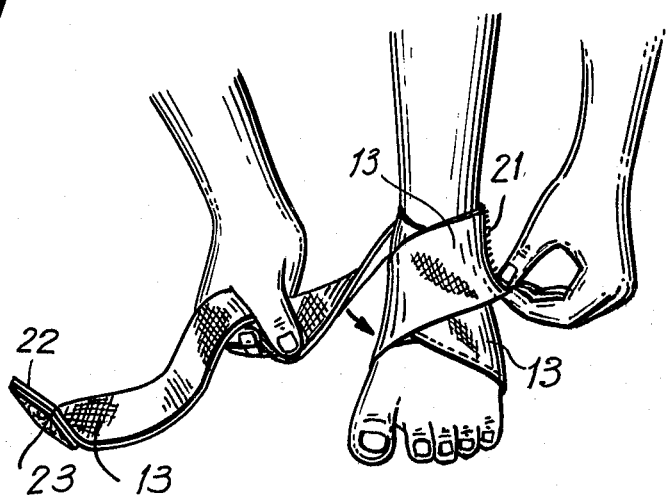
Figure 7:
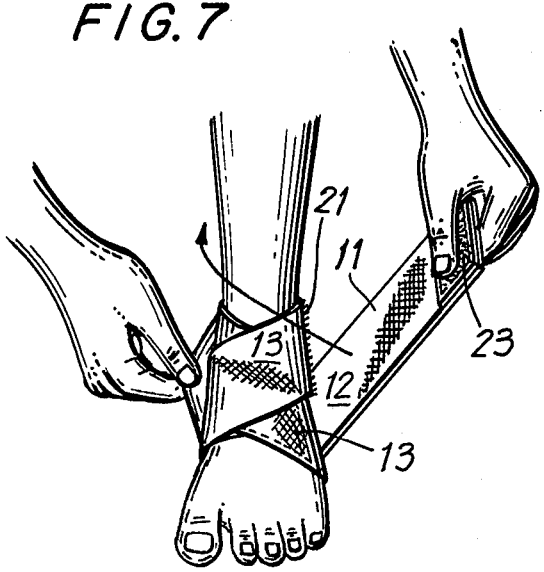
Figure 8:
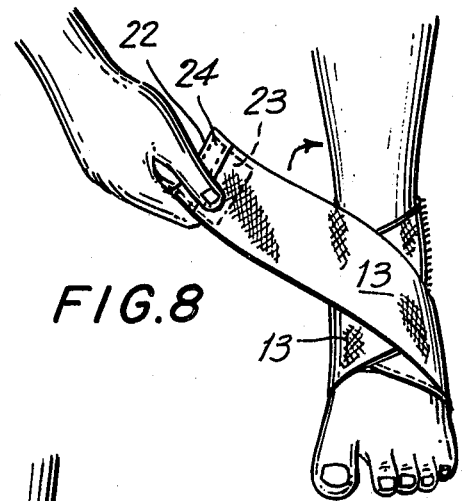
Figure 9:
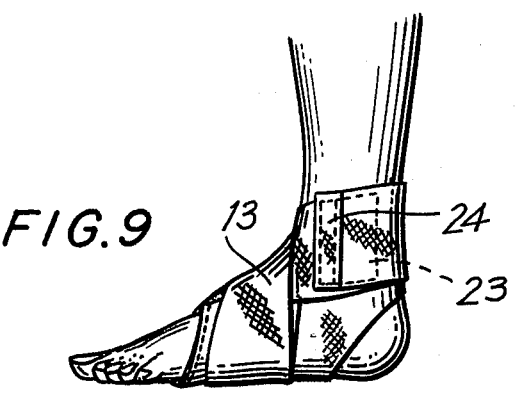

Reference is now made to FIGS. 3 through 9 wherein the manner in which an ankle is wrapped by the ankle wrap depicted in FIGS. 1 and 2 is illustrated in step by step fashion. As illustrated in FIG. 3, the wrapping operation is commenced by placing the male Velcro fastening tab 16 on the top of the foot's medial arch and by wrapping the medial arch with a nylon panel 15 so that the first Velcro fastening pad 20 is brought into releasable engagement with the male Velcro fastening tab 16 to define a first secure loop about the medial arch. After the first secure loop fastening is effected by the releasable engagement of the male Velcro fastener tab 16 to the female Velcro fastening pad 20 the remaining portion of the elongated panel is stretched taut and brought across the front of the ankle and around the back of the ankle to the position depicted in FIG. 4. Thereafter, as illustrated in FIGS. 4, 5 and 6, and once again in FIGS. 7, 8 and 9, the remaining free portion of the panel 11 continues to be stretched and after being brought around the back of the ankle is looped under the medial arch, up and across the front of the ankle and once again around the back of the ankle. Wrapping of the ankle is thereby effected without also effecting an alternating upward and downward criss-crossing of the ankle wrap at the front of the ankle, which criss-crossing can result in cutting off the circulation of blood to the lower foot. Moreover, as illustrated in FIG. 6, when the wrap is brought up and around the front and outside of the ankle and subsequently behind the ankle, the male Velcro fastening pad 21 is positioned to be engaged by the female Velcro pad 23, after the ankle, as illustrated in FIGS. 6, 7 and 8, is once again wrapped in the same manner described above, to wit, by stretching the remaining free portion of the panel and wrapping same around the back of the ankle, under the medial arch, up and across the front of the ankle and once again around the back of the ankle. When the end 22 of the panel is finally wrapped about the back of the ankle, the female Velcro pad 23 is releasably securably fastened to the male Velcro fastening pad 21 to thereby releasably lock the ankle wrap in position.

It is noted that the ankle wrap 10 illustrated in FIGS. 1 and 2 is for wrapping the left foot and that the angle at which the male Velcro fastening pad 16 is secured to the end 14 of the panel 12 is merely reversed for an ankle wrap designed to effect wrapping of the right ankle and foot in the aforedescribed manner.

Accordingly, the bracing effected by the instant invention is particularly designed to prevent rotation of the ankle about an imaginary horizontal front-to-back axis passing through the ankle joint. Rotation along such a front-to-back imaginary axis can result in sprains and hence the instant invention is directed to bracing the ankle against such rotation without restricting rotation about either a further horizontal, imaginary side-to-side axis through which the ankle joint rotates in walking and running or in a still further imaginary vertical axis in line with the lower leg, which rotation is utilized in pivoting and turning. Accordingly, an ankle wrap constructed in accordance with the instant invention is capable of effecting the same bracing of an ankle heretofore obtained by an adhesive "tape job" at a considerable reduction in expense due to the reusable nature of the ankle wrap.

It will thus be seen that the objects set forth, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An ankle wrap comprising in combination an elongated panel, first fastening means secured to a first elongated end portion of said panel, and second fastening means carried by said panel are positioned spaced apart from said first fastening means when said elongated portion of said panel between said first and second fastening means is wrapped around the arch portion of a foot said portion of said panel between said first and second fastening means being inelastic, and further fastening means disposed at the other elongated end portion of said elastic panel for releasably securably fastening said panel about said ankle and arch portion after said panel has been alternately wrapped about said ankle and arch portion in a predetermined manner said portion of said elongated panel between said second fastening means and third fastening means being elastic.

2. An ankle wrap as claimed in claim 1, wherein said further fastening means include a third fastening means carried on said panel and a fourth fastening means carried on said elastic panel at a predetermined distance from said third fastening means so that said fourth fastening means releasably engages said third fastening panel when said panel is wrapped in a predetermined manner.

3. An ankle wrap as claimed in claim 2, wherein said predetermined distance between said third and fourth fastening means is determined by the length of the panel when stretched and wrapped, measured from the inside of an ankle, around the back of an ankle, under a foot's medial aspect of the longitudinal arch, up and around the front of the foot, and around the back of the ankle to the inside of the ankle.

4. An ankle wrap as claimed in claim 2, wherein said first fastening means is a tab projecting from said first end of said panel.

5. An ankle wrap as claimed in claim 2, wherein said first and third fastening means are male Velcro fasteners and said second and fourth fastening means are female Velcro fasteners.

6. An ankle wrap as claimed in claim 5, wherein said elongated panel is provided with a front and a back surface, said first and third fastening means being mounted to said front surface and said second and fourth fastening means being mounted on said back surface.

7. An ankle wrap comprising in combination an elongated elastic panel having a first surface, a second surface, a first end and a second end, first fastening means secured to said first end of said panel, an inelastic panel secured to said first surface coextensive with said first end portion of said panel, second fastening means for releasably engaging said first fastening means, said second fastening means being secured to said first surface of said elastic panel so that said inelastic panel is disposed intermediate said respective first and second fastening means, and third fastening means secured to the second end of said panel for releasably securing said second end of said panel to an intermediate portion of said panel.

8. An ankle wrap as claimed in claim 7 and including a fourth fastening means secured to said second surface of said panel at a predetermined distance from said third fastening means, said fourth fastening means being adapted to be releasably engaged by said third fastening means.

9. An ankle wrap as claimed in claim 8, wherein said first fastening means is a tab secured to the second surface of said panel proximate to the first end thereof and said third fastening means is secured to the first surface of said panel.

10. An ankle wrap as claimed in claim 9, wherein said first and fourth fastening means are male Velcro fasteners and said second and third fastening means are female Velcro fasteners.

11. A method of wrapping an ankle utilizing an ankle wrap comprised of an elastic wrapping panel and an inelastic end panel at a first end of the elastic wrapping panel comprising the steps of looping and fastening said inelastic panel about said medial aspect of the longitudinal arch of a foot so that the elastic panel is extending in an upward direction, and wrapping and stretching said elastic panel around the front of an ankle, behind the ankle and under the foot's medial aspect of the longitudinal arch at least two times in order to effectively brace the ankle.

12. A method of wrapping an ankle as claimed in claim 11 including the additional step of releasably fastening the other end of the elastic panel to an intermediate portion of the elastic panel wrapped around the ankle after said elastic panel has been wrapped about the ankle and medial aspect of the longitudinal arch at least twice.

* * * * *